United States Patent
Yang et al.

(10) Patent No.: US 9,889,212 B2
(45) Date of Patent: Feb. 13, 2018

(54) PREPARATION METHOD FOR MAGNETIC COMPOSITE FOR TREATING AND DIAGNOSING CANCER

(71) Applicant: Industry-Academic Cooperation Foundation, Yonsei University, Seoul (KR)

(72) Inventors: Jae Moon Yang, Seoul (KR); Jin Suck Suh, Seoul (KR); Seung Joo Haam, Seoul (KR); Eu Gene Lee, Seoul (KR); Yoo Chan Hong, Seoul (KR); Min Hee Ku, Seoul (KR); Dan Heo, Seoul (KR); Seung Yeon Hwang, Seoul (KR); Yong Min Huh, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 15/120,064

(22) PCT Filed: Feb. 17, 2015

(86) PCT No.: PCT/KR2015/001608
§ 371 (c)(1),
(2) Date: Aug. 18, 2016

(87) PCT Pub. No.: WO2015/126146
PCT Pub. Date: Aug. 27, 2015

(65) Prior Publication Data
US 2017/0056533 A1    Mar. 2, 2017

(30) Foreign Application Priority Data
Feb. 20, 2014   (KR) .................. 10-2014-0019908

(51) Int. Cl.
*A61K 49/12* (2006.01)
*A61K 41/00* (2006.01)
*A61K 49/18* (2006.01)
*A61B 5/055* (2006.01)

(52) U.S. Cl.
CPC .......... *A61K 49/12* (2013.01); *A61K 41/0052* (2013.01); *A61K 49/1818* (2013.01); *A61K 49/1854* (2013.01); *A61K 49/1887* (2013.01); *A61B 5/055* (2013.01)

(58) Field of Classification Search
USPC ....................................... 556/138, 141, 143
See application file for complete search history.

(56) References Cited

U.S. PATENT DOCUMENTS

2013/0183249 A1 *   7/2013   Haam .................... A61K 39/44
                                                      424/9.322

FOREIGN PATENT DOCUMENTS

| KR | 2009-0093169 A | 9/2009 | |
|----|----------------|--------|---|
| KR | 2010-0030264 A | 3/2010 | |
| KR | 2011-0059369 A | 6/2011 | |
| WO | WO2012015125 A1 * | 2/2012 | ............ A61K 9/127 |

OTHER PUBLICATIONS

Hwang Seung Yeon et al., "The 111th General Meeting of the Korean Chemical Society," Poster Presentation dated Apr. 17, 2013.

* cited by examiner

*Primary Examiner* — Pancham Bakshi
(74) *Attorney, Agent, or Firm* — Marshall, Gerstein & Borun LLP

(57) ABSTRACT

A preparation method for a magnetic composite for treating and diagnosing cancer. The method may include a step of pyrolyzing a precursor of a magnetic nanoparticle in the presence of a conjugated polymer. The preparation method for a magnetic composite can produce a magnetic composite economically and efficiently because a magnetic composite comprising a magnetic nanoparticle coated with a conjugated polymer can be prepared by a single process.

8 Claims, 7 Drawing Sheets

[FIG. 1]
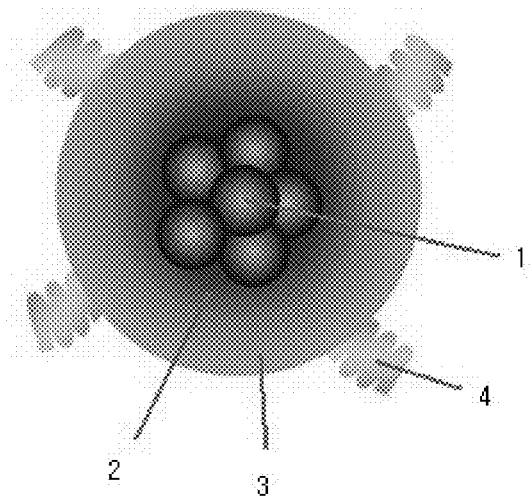
[FIG. 2]
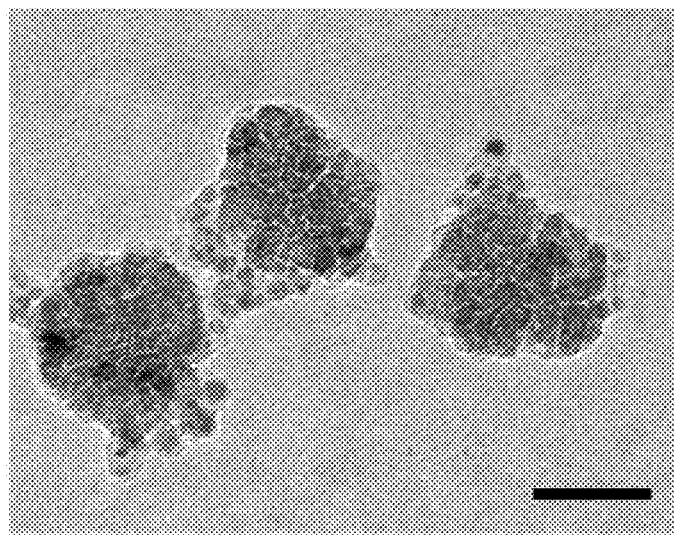

[FIG. 3]
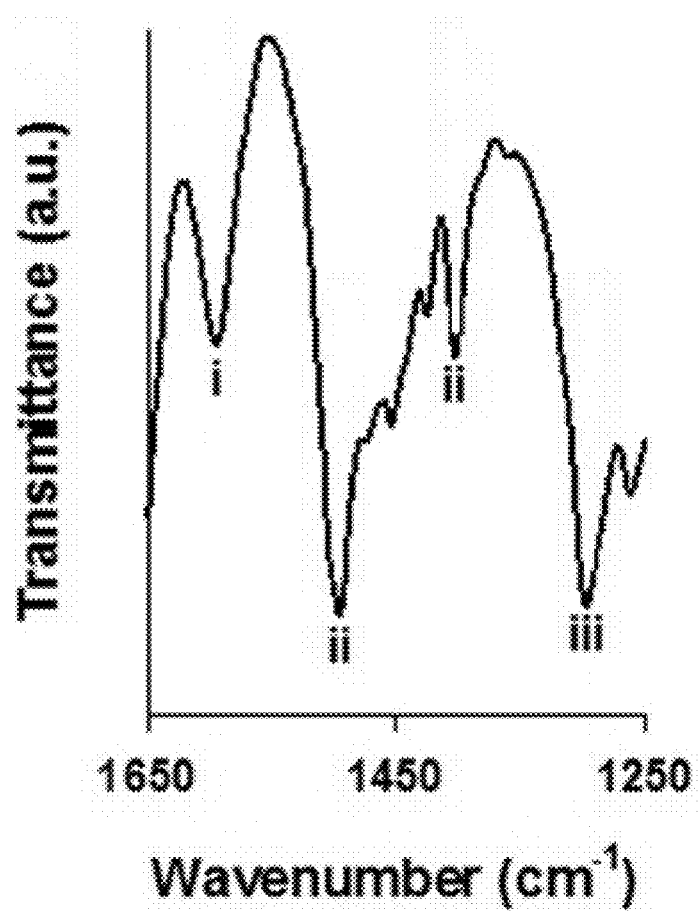

[FIG. 4]
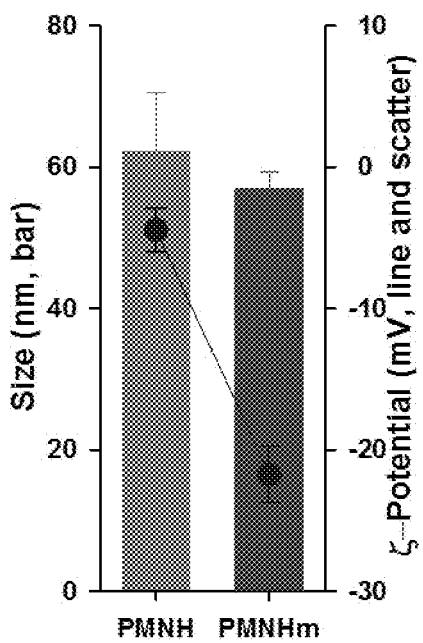
[FIG. 5]
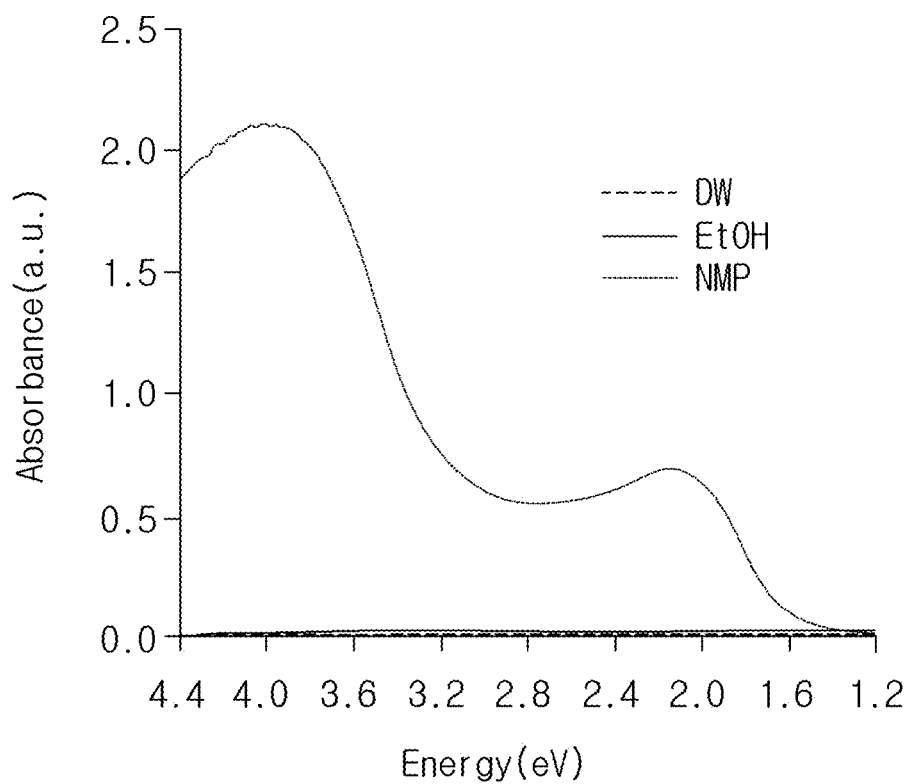

[FIG. 6]
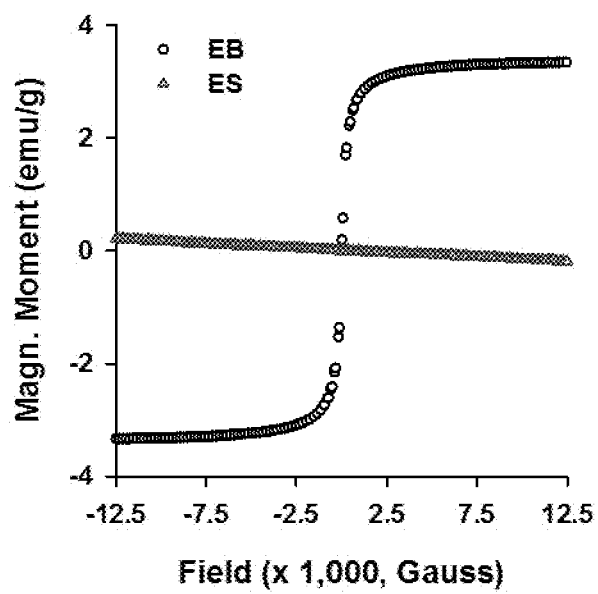
[FIG. 7]
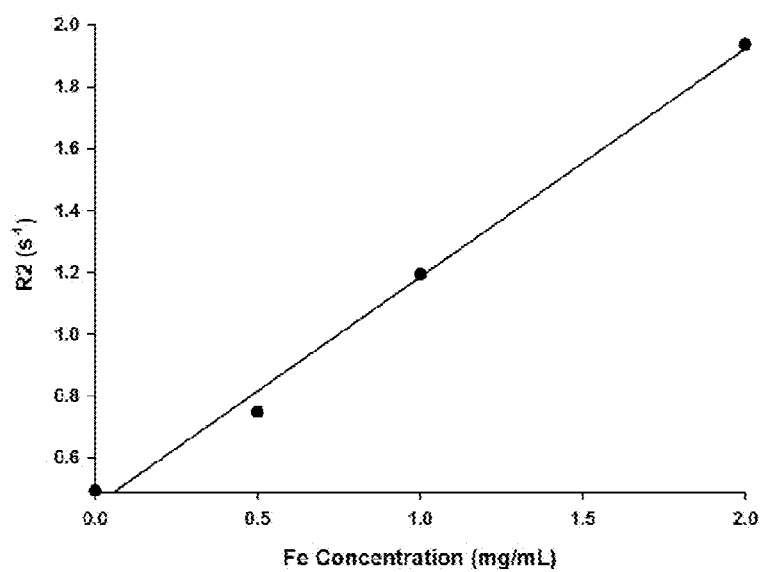

[FIG. 8]
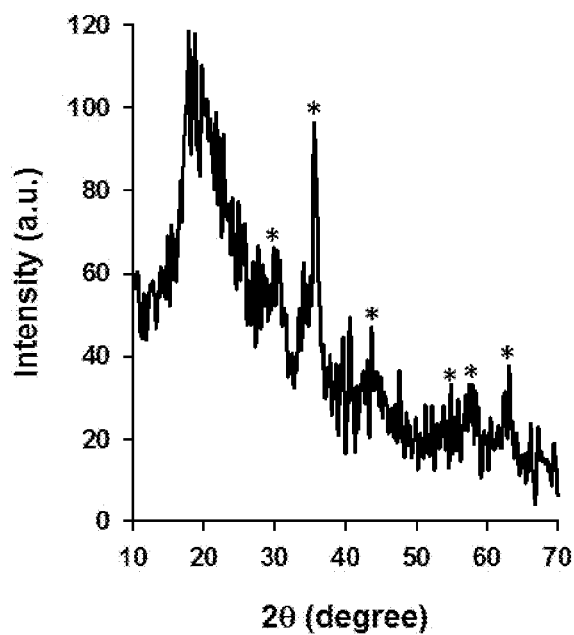
[FIG. 9]
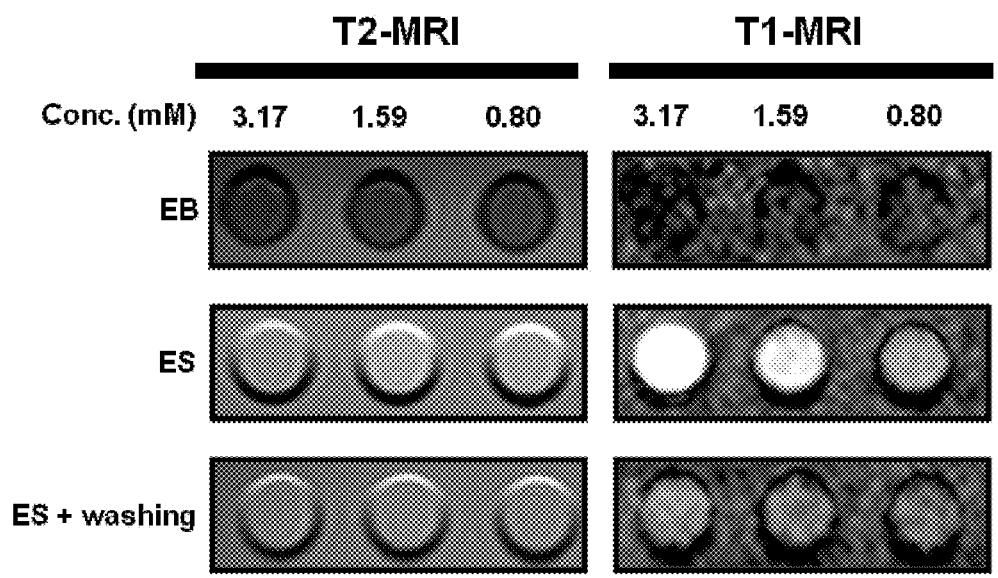

[FIG. 10]
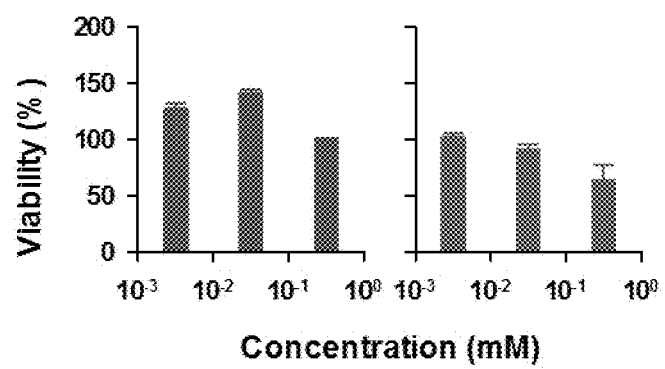
[FIG. 11]
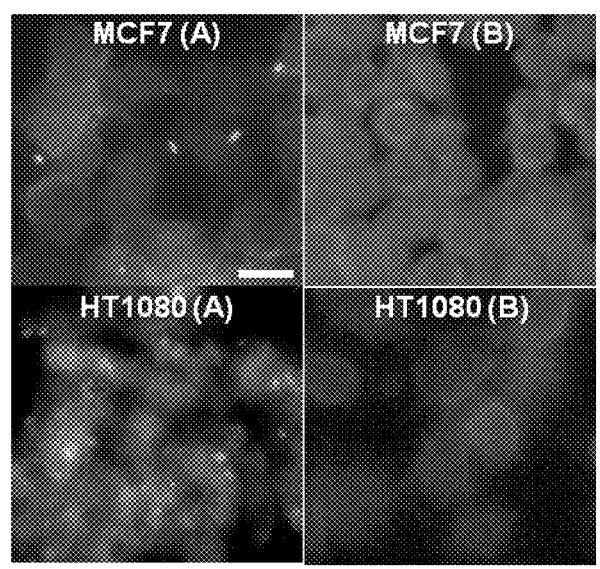

[FIG. 12]
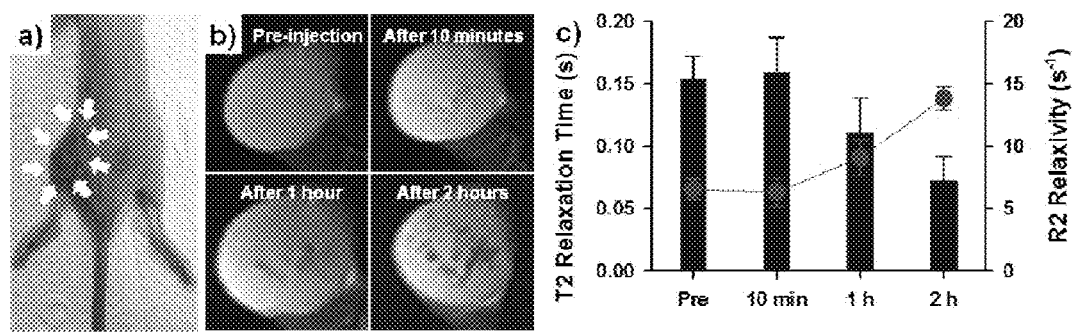
[FIG. 13]
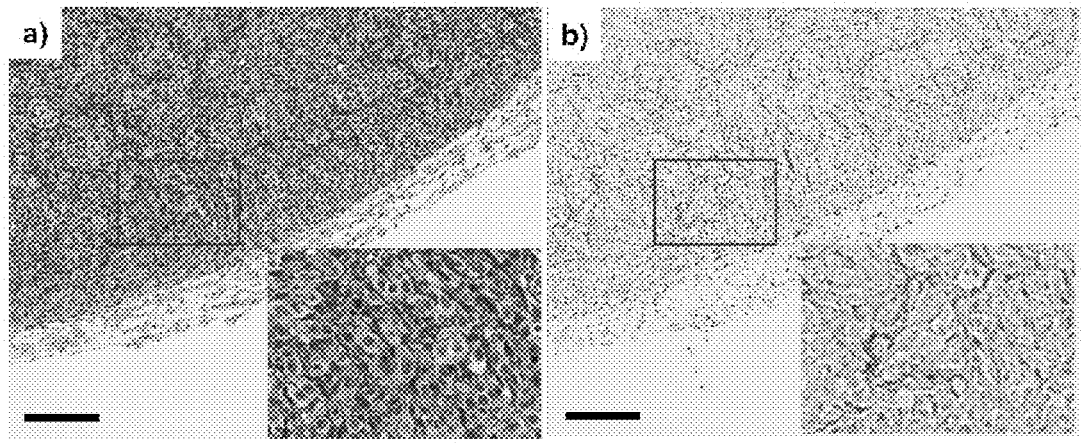

PREPARATION METHOD FOR MAGNETIC COMPOSITE FOR TREATING AND DIAGNOSING CANCER

CROSS-REFERENCE TO RELATED APPLICATIONS

This application is a national stage application under 35 U.S.C. § 371 and claims the benefit of priority of international application no. PCT/KR2015/001608, filed Feb. 17, 2015, which claims the benefit of priority under 35 U.S.C. §. 119 of Korean patent application no. 10-2014-0019908, filed Feb. 20, 2014, the entire contents of each being hereby incorporated herein by reference, in its entirety and for all purposes.

TECHNICAL FIELD

The present disclosure relates to a method of preparing a magnetic composite for treating and diagnosing cancers and a magnetic composite for treating and diagnosing cancers prepared by the method.

BACKGROUND

Cancer remains the most dangerous disease which threatens humans. Surgery, which is one method of treating cancer, causes serious side effects because normal cells adjacent to cancer cells are inevitably removed with the cancer cells. Accordingly, target treatment is considered the most ideal method of treating cancers.

A great deal of research is underway on photothermal therapy targeting a diseased part and offering local treatment, as a cancer targeted method. However, photothermal therapy has a drawback of difficulty of anatomically accurate diagnosis. In order to solve this problem, a new cancer therapy strategy, so-called "theragnosis" having therapeutic and diagnosis functions has been developed (Non-Patent Document 1). However, theragnosis involves a complicated process for preparing substances for treating and diagnosing cancers due to multi-functions and has a limitation in providing the substances in an efficient manner.

One document that serves as background to the present application is Angew. Chem. Int. Ed. Magnetic Nanoparticles: Synthesis, Protection, Functionalization, and Application, 2007, 46, 1222-1244.

SUMMARY OF THE DISCLOSURE

Therefore, it is one object of the present disclosure to provide a method of preparing a magnetic composite for treating and diagnosing cancer which can offer a magnetic composite for photothermally treating and diagnosing cancers in a simple manner.

It is another object of the present disclosure to provide a magnetic composite for treating and diagnosing cancers prepared by the method.

In accordance with an aspect of the present disclosure, the above and other objects can be accomplished by the provision of a method of preparing a magnetic composite for treating and diagnosing cancers including thermally decomposing a precursor of magnetic nanoparticles in the presence of a conjugated polymer.

The precursor of magnetic nanoparticles may, for example, include metal acetylacetonate, metal cupferronate, metal carbonyl, metal chloride, metal sulfide or a mixture thereof.

The conjugated polymer may be present in an amount of 1 to 1,000 parts by weight, with respect to 100 parts by weight of the magnetic nanoparticles precursor.

In an embodiment, the thermal decomposition may include heating a solution containing the conjugated polymer and the precursor of magnetic nanoparticles at a temperature of 100 to 500° C.

In an embodiment, the thermal decomposition may include pre-heating the solution containing the conjugated polymer and the precursor of magnetic nanoparticles at a temperature of 100 to 300° C. and heating at a temperature of 200° C. to 500° C.

The method may further include processing the magnetic composite after the thermal decomposition.

The processing may include treating the magnetic composite with a surfactant, or mixing the magnetic composite with a bio-ligand.

In accordance with another aspect of the present disclosure, provided is a magnetic composite for treating and diagnosing cancers including a conjugated polymer and magnetic nanoparticles, wherein the magnetic nanoparticles are coated with the conjugated polymer and the conjugated polymer was not separated from the magnetic nanoparticles when the magnetic composite is dissolved in 1-methyl-2-pyrrolidone.

The conjugated polymer may have a weight average molecular weight of 500 to 100,000 g/mol. In addition, the conjugated polymer may, for example, include polyaniline, polyacetylene, polypyrrole, polythiophene, poly(p-phenylene vinylene, poly(1,4-phenylene sulfide), poly(fluorenylene ethynylene), a mixture thereof, or a derivative thereof. The magnetic nanoparticles may include metal oxide.

In an embodiment, the magnetic composite may be processed with a surfactant present on the surface of the magnetic composite and a bio-ligand linked to the magnetic composite through the surfactant.

With the method of preparing a magnetic composite according to an embodiment, it is possible to prepare a magnetic composite including magnetic nanoparticles coated with a conjugated polymer by one-pot synthesis and thus obtain the magnetic composite in an economical and efficient manner.

BRIEF DESCRIPTION OF DRAWINGS

The above and other objects, features and other advantages of the present disclosure will be more clearly understood from the following detailed description taken in conjunction with the accompanying drawings, in which:

FIG. 1 is a schematic view showing an exemplary target-specific magnetic composite;

FIG. 2 is a TEM image showing a magnetic composite prepared in Preparation Example 1;

FIG. 3 is a FT-IR spectrum showing the magnetic composite prepared in Preparation Example 1;

FIG. 4 is a graph showing a hydrodynamic size and zeta potential of the magnetic composite prepared in Preparation Example 1 and a hydrodynamic size and zeta potential of a target-specific magnetic composite prepared in Example 1;

FIG. 5 is a graph showing a absorbance of the magnetic composite prepared in Preparation Example 1;

FIG. 6 shows data associated with sensitivity to magnetic field of the magnetic composite prepared in Preparation Example 1;

FIG. 7 shows data associated with MR imaging of the magnetic composite prepared in Preparation Example 1;

FIG. 8 shows X-ray diffraction patterns of the target-specific magnetic composite prepared in Example 1;

FIG. 9 shows data associated with MR imaging of the target-specific magnetic composite prepared in Example 1;

FIG. 10 shows data associated with cell viability test to evaluate cytotoxicity of the target-specific magnetic composite prepared in Example 1;

FIG. 11 shows data to evaluate target-specificity and redox state detection of the target-specific magnetic composite prepared in Example 1;

FIG. 12 is a first image (labeled "a)") showing a mouse in which HT 1080 cells are injected into the proximal thigh in Test Example E; a series of images (labeled "b)") is T2-weighted MR images before injection of the target-specific magnetic composite, and 10 minutes, one hour and two hours after injection of the target-specific magnetic composite; and a graph (labeled "c)") showing T2 relaxation time and R2 relaxivity measured when obtaining the image labeled "b)"; and FIG. 13 is an image (labeled "a)") showing results of H&E staining in cancer tissues and an image (labeled "b)") showing results of Prussian blue staining in cancer tissues.

DETAILED DESCRIPTION

Hereinafter, the present embodiments will be described in detail.

The method of preparing a magnetic composite for treating and diagnosing cancers according to an embodiment includes thermally decomposing a precursor of magnetic nanoparticles in the presence of a conjugated polymer.

The magnetic composite may be a nano-composite. The term "nano-composite" as used herein means a nanometer scale substance which includes a combination of an organic substance with an inorganic substance. The nanometer scale, for example, means about 1 to 1,000 nm. The magnetic composite that can be used in the treatment of cancers may be a magnetic composite capable of photothermally treating cancers. The magnetic composite capable of photothermally treating cancers may absorb light in a near-infrared (NIR) area which does not cause damage to normal cells and emit a great amount of heat upon absorption of light. In particular, the magnetic composite may not normally absorb light in a near-infrared region, but may absorb light in the near-infrared region near cancer cells. That is, when incorporated into cells, the magnetic composite is doped with a dopant present in the cells and absorbs light in a near-infrared region. Accordingly, the magnetic composite can specifically remove only cancer cells containing a dopant in cells and does not cause damage to normal cells or blood vessels while removing the cancer cells. The magnetic composite capable of photothermally treating cancers based on such a principle can be incorporated into the human body by direct administration to cancer cells or cancer tissues as well as intravascular administration using an injection. The therapeutic function of cancers can be secured by a conjugated polymer of the magnetic composite.

The magnetic composite that can be used in the diagnosis of cancers may be a magnetic composite which is capable of diagnosing cancers by a magnetic resonance imaging (MRI) device. Such a cancer diagnosis function can be secured by magnetic nanoparticles of the magnetic composite.

In particular, the magnetic composite is used for treating and diagnosing cancers, more specifically, is used for monitoring removal of cancers while photothermally treating cancers, or is used for diagnosing removal of cancers after photothermally treating cancers.

In accordance with the preparation method of the magnetic composite, the magnetic composite, which enables photothermal therapy of cancers and diagnosis by magnetic resonance imaging, can be obtained by one-pot synthesis and is thus economical and efficient. In addition, the magnetic composite prepared by a simple process has superior functions of photothermal therapy and diagnosis of cancers to conventional photothermal therapy agents and contrast agents. More specifically, the preparation method can provide a magnetic composite containing magnetic nanoparticles coated with a conjugated polymer by a one-pot process, based on thermal decomposition of a precursor of magnetic nanoparticles in the presence of the conjugated polymer.

The magnetic nanoparticles may be magnetic so that they can be detected by magnetic resonance imaging. The magnetic nanoparticles are commonly obtained by a mixture of a precursor of magnetic nanoparticles with a surfactant. However, the preparation method can provide a multifunctional magnetic composite by a one-pot process because it is designed to produce magnetic nanoparticles and at the same time, coat the magnetic nanoparticles with a conjugated polymer enabling photothermal therapy of cancers.

The magnetic nanoparticles contained in the magnetic composite may be selected from those that can be detected by magnetic resonance imaging and is for example metal oxide. Examples of the metal oxide include iron oxide, manganese oxide, cobalt oxide, nickel oxide, chromium oxide, or a mixture thereof. The precursor of magnetic nanoparticles can be converted into the aforementioned magnetic nanoparticles by thermal decomposition and can be selected from those used in the art without any limitation. Examples of the precursor of magnetic nanoparticles include metal acetylacetonate, metal cupferronate ($C_6H_5N(NO)O^-$), metal carbonyl, metal chloride, metal sulfide or a mixture thereof. The metal may be bivalent or trivalent iron (Fe), manganese (Mn), cobalt (Co), nickel (Ni), gadolinium (Gd), molybdenum (Mo) or the like.

The conjugated polymer functions as a ligand for the precursor during thermal decomposition of the magnetic nanoparticle precursor to aid in preparation of the magnetic nanoparticles and is coated on magnetic nanoparticles during preparation of magnetic nanoparticles, thereby simultaneously preparing the magnetic nanoparticles and the magnetic composite.

In particular, a magnetic composite enabling photothermal therapy of cancers can be provided by using a conjugated polymer which absorbs near-infrared light based on doping in cells. Examples of the conjugated polymer include polyaniline, polyacetylene, polypyrrole, polythiophene, poly(p-phenylene vinylene, poly(1,4-phenylene sulfide), poly(fluorenylene ethynylene), mixtures thereof, derivatives thereof and the like.

The conjugated polymer functions as a ligand for the precursor of magnetic nanoparticles upon preparation of magnetic nanoparticles and has a suitable molecular weight to form the magnetic composite by coating the magnetic nanoparticles with the conjugated polymer. For example, the conjugated polymer has a weight average molecular weight of 500 to 100,000 g/mol to maximize the effects described above.

In an embodiment, the conjugated polymer may be polyaniline. Polyaniline is biocompatible so that it is used as an electroactive material for research of cell proliferation. In addition, when polyaniline is doped into cells, polyaniline exhibits shift of optical-absorbance peak to a near-infrared region and emits heat energy sufficient to remove cancer cells upon application of near-infrared light. More specifically, polyaniline is converted from an emeraldine base to an emeraldine salt due to acidity or various doping materials of cells and emits a great amount of heat upon application of near-infrared light to the emeraldine salt form of polyaniline. Accordingly, polyaniline can be used as the conjugated polymer in order to prepare a magnetic composite that is capable of selectively photothermally treating only cancer cells while being not harmful to the human body.

In the thermal decomposition, the conjugated polymer and the precursor of magnetic nanoparticles may be used in suitable amounts depending on functions of the magnetic composite. In an embodiment, to secure superior cancer treatment and diagnosis functions, the conjugated polymer may be used in an amount of 1 to 1,000 parts by weight, 1 to 500 parts by weight, 1 to 200 parts by weight, 10 to 200 parts by weight, 10 to 150 parts by weight or 30 to 150 parts by weight, with respect to 100 parts by weight of the precursor of magnetic nanoparticles. When the conjugated polymer is present in an amount of less than the range defined above, diagnosis by magnetic resonance imaging may be insufficient and, when the conjugated polymer is present in an amount exceeding the range, uniformity and stability of particles are deteriorated and a magnetic composite having low magnetic resonance imaging diagnosis efficiency may be obtained.

The thermal decomposition may include heating a solution containing the conjugated polymer and the precursor of magnetic nanoparticles. The temperature and time for heating the solution may be suitably controlled depending on the types and contents of the conjugated polymer and magnetic nanoparticle precursor. For example, thermal decomposition may include heating the solution at a temperature of 100 to 500° C., 100 to 400° C., 100 to 350° C., 150 to 500° C., 150 to 400° C. or 150 to 350° C. In addition, the thermal decomposition may include heating the solution at the temperature for about 10 minutes to 10 hours, about 10 minutes to 5 hours, about 10 minutes to 3 hours, or about 30 minutes to 2 hours. When the heating temperature and time in the thermal decomposition are less than the range defined above, the yield of magnetic nanoparticles is deteriorated and magnetic nanoparticles with a uniform size and good magnetism cannot be produced, and when the heating temperature and time of the solution exceed the range, the conjugated polymer is damaged and it is difficult to produce the targeted magnetic composite.

In an embodiment, the thermal decomposition may include pre-heating the solution. More specifically, the thermal decomposition may include pre-heating the solution at a temperature of 100 to 300° C. and heating at a temperature of 200° C. to 500° C. or 250° C. to 500° C. In this case, the pre-heating temperature may be controlled to be lower than the heating temperature. The pre-heating time of the solution can be controlled to 30 to 80%, 40 to 70%, 50 to 70% or 60 to 70% of the total heating time. As described above, when the solution is pre-heated and then heated, uniform magnetic composite can be synthesized. By thermal decomposition using the solution containing the conjugated polymer and the precursor of magnetic nanoparticles, a magnetic composite containing the conjugated polymer and magnetic nanoparticles coated therewith can be obtained.

The magnetic composite may include one or more magnetic nanoparticles. The magnetic nanoparticles may have a mean diameter of 1 to 100 nm. In addition, the distribution degree of the mean diameter the magnetic nanoparticles may be 0.1 to 10 nm.

The magnetic composite has a structure in which one or more magnetic nanoparticles are incorporated in a matrix including a conjugated polymer. Referring to the schematic view shown in FIG. 1, the magnetic composite may have a structure in which magnetic nanoparticles (1) are entangled with conjugated polymer chains (2) so that the magnetic nanoparticles (1) are trapped in the matrix of the conjugated polymer (2).

The mean diameter of the magnetic composite formed by the preparation method may be 30 to 500 nm. In addition, the distribution degree of the mean diameter of the magnetic nanoparticles may be 0.3 to 50 nm. When the mean diameter of the magnetic composite is less than the range defined above, non-specific cellular uptake and imaging may be difficult, and when the mean diameter of the magnetic composite exceeds the range, the magnetic composite may be unstable in an aqueous phase and particles may not be efficiently circulated in vivo.

The magnetic composite absorbs near-infrared light when doped in cells. The doped magnetic composite, for example, absorbs light at a wavelength of 600 to 1,100 nm and emits a great amount of heat. In an embodiment, in a case in which the magnetic composite includes iron magnetic particles containing polyaniline, a temperature of less than about 1° C. increases upon application of light having a wavelength within the range to pure water, whereas a temperature of about 4° C. or greater increases regardless of EB or ES phase upon application of the same light to the magnetic composite. Accordingly, the magnetic composite can remove cancers in a local area without causing damage to normal cells. In addition, the magnetic composite can diagnose the state of cancers using the most generally used magnetic resonance imaging device during or after treatment of cancers due to magnetic nanoparticles.

The preparation method may further include processing the magnetic composite after thermal decomposition in order to prepare a magnetic composite optimal for treatment and diagnosis of cancers. Throughout the specification, both "conjugated polymer-coated magnetic nanoparticles" formed after thermal decomposition and "magnetic composite containing a surfactant and/or a bio-ligand" formed after thermal decomposition and processing are magnetic and include a mixture of an organic substance and an inorganic substance, and are thus referred to as a "magnetic composite. However, to distinguish a non-processed magnetic composite from a processed magnetic composite, hereinafter, the former will be referred to as a "first magnetic composite" and the latter will be referred to as a "second magnetic composite". In addition, among the processed magnetic composites, the processed magnetic composite processed with a bio-ligand, or a surfactant and a bio-ligand will be referred to as an "water-soluble magnetic composite" and the processed magnetic composite processed with a surfactant will be referred to as a "target-specific magnetic composite".

A therapeutic agent or contrast agent or the like, which is used in vivo such as treatment and diagnosis of cancers, requires high dispersibility in an aqueous phase. Accordingly, the first magnetic composite prepared during the thermal decomposition can be converted into a water-soluble magnetic composite by processing. The processing for converting the first magnetic composite to the water-soluble magnetic composite may include treating the first magnetic composite with a surfactant. The treating the first magnetic composite with the surfactant may be carried out by stirring a mixed solution of the first magnetic composite and the surfactant. The first magnetic composite and surfactant may be stirred at room temperature for a suitable time determined depending on the content of the first magnetic composite. As used herein, the term "room temperature" means a non-treated temperature which is subjected to neither increase nor decrease and, for example, means about 15 to 35° C. or 20 to 25° C.

Examples of the surfactant useful for processing include carboxymethylcellulose, polyvinyl alcohol, polyacrylamide, polyethyleneimine, polyamidoamine, polyethylene glycol, polylactic acid, polyacrylic acid, polycaprolactone, polystyrene sulfonate, polyhydroxy (meth)acrylate, chitosan, polysorbate 80 (TWEEN 80), polyvinyl sulfonic acid, Textran, sodium cholate hydrate, n-octyl glucoside, octylthioglucoside, n-octanoyl-N-methyl glucamine, N-nonanoyl-N-methyl glucamine, quillaja bark-derived saponin, polyoxyethylene sorbitan monolaurate, sodium dodecyl sulfate, tetramethylammonium hydroxide solution, hexadecyltrimethylammonium bromide (CTAB), didodecyldimethylammonium bromide (DMAB), N,N-bis(3-D-gluconamidopropyl)deoxycholamide (deoxy-BIGCHAP), N,N-bis (3-D-gluconamidopropyl)cholamide (BIGCHAP), polyethylene glycol dodecyl ether, Pluronic F-68, Triton X-100, Triton X-114, Tween 40, Igepal CA-630, Igepal CO-210, Igepal CO-520, Igepal CO-630, Igepal CO-720, Igepal CO-890, Igepal DM-970, Igepal CA-210, Igepal CA-520, Igepal CA-630, N-decanoyl-N-methyl glucamine, nonylphenyl-polyethylene glycol, Brij 76, Brij 58, Brij 35P, Brij 30, cyclohexylmethyl-β-D-maltoside (Cymal-1), 2-cyclohexylethyl-β-D-maltoside (Cymal-2), 5-cyclohexylpentyl-β-D-maltoside (Cymal-5), 6-cyclohexylhexyl-β-D-maltoside (Cymal-6), digitonin, decyl-β-D-maltopyranoside, lauryl-β-D-maltoside (DDM), n-hexadecyl-β-D-maltoside, undecyl-β-D-maltoside, decyl-β-1-thiomaltopyranoside, decyl-β-D-thioglucopyranoside, decyl dimethyl phosphine oxide, dodecyl dimethyl phosphine oxide or mixtures thereof. These surfactants may be modified upon use, if necessary.

The water-soluble magnetic composite treated with a surfactant can exhibit water-solubility by which the surfactant is disposed on the surface of the conjugated polymer-coated magnetic nanoparticles. As shown in FIG. 1, the water-soluble magnetic composite may have a structure in which a surfactant (3) is disposed on the surface of the first magnetic composite including magnetic nanoparticles (1) entangled with conjugated polymer chains (2).

The magnetic composite can be prepared for treating or diagnosing a specific cancer. For this purpose, the processing may include mixing the first magnetic composite with a bio-ligand. The mixing the first magnetic composite with the bio-ligand may be carried out by stirring a solution containing the first magnetic composite and the bio-ligand. The solution containing the first magnetic composite and the bio-ligand may be stirred at room temperature for a suitable time depending on the content of the first magnetic composite.

The bio-ligand is a target-specific substance and is suitably selected depending on the type of cancers to be treated and diagnosed. Examples of the bio-ligand include antigens, antibodies, RNA, DNA, aptamers, hapten, avidin streptavidin, neutravidin, protein A, protein G, lectin, selectin or radioisotope-marked substances. In an embodiment, when a magnetic composite for treating and diagnosing fibrosarcoma HT 1080 cancer cells is prepared, the bio-ligand may be membrane type-1 matrix metalloproteinase (MT1-MMP) targetable peptide.

A method of linking the bio-ligand to the first magnetic composite may be selected from various methods well-known in the art depending on the bio-ligand. In an embodiment, the bio-ligand may be mixed with the water-soluble magnetic composite and linked to first magnetic composite by the surfactant. Accordingly, as shown in FIG. 1, the target-specific magnetic composite may have a structure in which the bio-ligand (4) is linked to the first magnetic composite by the surfactant (3). When the bio-ligand is linked to the first magnetic composite by such a method, a modified surfactant may be used as the surfactant to physically or chemically link the bio-ligand to the first magnetic composite.

The target-specific magnetic composite formed by the preparation method can be used for local treatment of specific cancers. In addition, by using the target-specific magnetic composite, the treatment condition of cancers can be diagnosed by a magnetic resonance imaging device and efficient treatment of cancers is thus possible.

The magnetic composite for treating and diagnosing cancers according to another embodiment is obtained by the preparation method as described above. The magnetic composite includes a conjugated polymer and magnetic nanoparticles, and has a structure in which the magnetic nanoparticles are coated with the conjugated polymer. The detailed ingredients contained in the magnetic composite and characteristics thereof have been described above.

Although the magnetic composite prepared by the method described above is dissolved in 1-methyl-2-pyrrolidone (NMP), the conjugated polymer is not separated from magnetic nanoparticles. If the composite is prepared by preparing the magnetic nanoparticles and then coating the same with a polymer, magnetic nanoparticles are separated from the polymer when the composite is dissolved in a NMP solvent. For this reason, the magnetic composite obtained by the aforementioned method is widely useful because it can maintain the original form upon dissolution in various organic solvents such as NMP, and is very suitable for treating and diagnosing cancers because the magnetic nanoparticles are not separated in vivo from the conjugated polymer.

In addition, the magnetic nanoparticles contained in the magnetic composite prepared by the method described above are formed by thermal decomposition so that they have uniform size and high magnetism. When coprecipitation including slowly dropping two or more precursors for magnetic particles into an about 8° C. basic solution is used for preparing the magnetic particles, the magnetism of the magnetic particles is deteriorated and is not uniform due to non-uniform size of magnetic particles.

The magnetic composite can be processed into a water-soluble form for treating and diagnosing cancers. The water-soluble magnetic composite may include a surfactant present on the surface of the first magnetic composite. The detailed ingredients contained in the water-soluble magnetic composite and characteristics thereof have been described above.

In addition, the magnetic composite may be processed into a target-specific form. The target-specific magnetic composite may include a bio-ligand present on the surface of the first magnetic composite.

The target-specific magnetic composite can secure both water-solubility and target-specificity because the bio-ligand is linked to the first magnetic composite by the surfactant. The detailed ingredients contained in the target-specific magnetic composite and characteristics thereof have been described above.

The magnetic composite for treating and diagnosing cancers may be contained in a pharmaceutically acceptable carrier. The pharmaceutically acceptable carrier may include carriers and vehicles commonly used in the medicine. Examples of the carriers include ion exchange resins, alumina, stearate, lecithin, serum proteins (e.g., human serum albumin, etc.), buffer substances (for example, various phosphates, glycine, sorbic acid, potassium sorbate, partial glyceride mixtures of saturated vegetable fatty acids, etc.), water, electrolytes (e.g., protamine sulfate, disodium hydrogen phosphate, sodium hydrogen phosphate, sodium chloride, zinc salts, etc.), colloidal silica, magnesium trisilicate, polyvinyl pyrrolidone, cellulose-based substrates, polyethylene glycol, sodium carboxymethylcellulose, polyarylates, waxes, polyethylene glycol, lanolin and the like.

The magnetic composite for treating and diagnosing cancers may be used as an aqueous solution for parenteral administration. Examples of the aqueous solution include Hank's solution, Ringer's solution and buffer solutions such as physically buffered saline.

In addition, the magnetic composite for treating and diagnosing cancers may be used as a sterile injection preparation. The magnetic composite may be formulated as a sterile injection preparation according to a method well-known in the art. However, the use method of the magnetic composite is not limited to methods described above and is selected from various methods well-known in the art.

Hereinafter, examples according to the present disclosure will be described in detail to such an extent that a person having ordinary knowledge in the field to which the disclosure pertains can easily carry out the disclosed embodiments. However, the presently disclosed embodiments can be realized in various forms and is not limited to the examples stated herein.

Preparation Example A: Preparation of Magnetic Composite and Modified Surfactant Preparation Example 1

1 g of polyaniline having a weight average molecular weight of about 5,000 g/mol was dissolved in 20 mL of 1-methyl-2-pyrrolidone. In addition, 706.4 mg of iron (III) acetylacetonate was dissolved in 20 mL of benzyl ether. The prepared two solutions were mixed, the resulting mixed solution was pre-heated at an elevated temperature of 200° C. for one hour and heated at an elevated temperature of 300° C. for 30 minutes. The heated mixed solution was allowed to cool at room temperature for 3 hours. Sequentially, the product was washed with excess ethanol and centrifuged at a rate of 3,000 rpm for 10 minutes to isolate a precipitate. The isolated precipitate was dispersed in ethanol again and centrifuged three times. During the final centrifugation, the precipitate was isolated to obtain a magnetic composite including magnetic nanoparticles coated with polyaniline. The magnetic composite was dispersed in 1-methyl-2-pyrrolidone which was used in the subsequent step.

Preparation Example 2

1 g of TWEEN 80 (Sigma-Aldrich) was dissolved in 50 mL of dichloromethane. Then, 0.709 g of N,N'-dicyclohexylcarbodiimide (DCC), 0.420 g of 4-(di-methylamino)pyridine (DMAP), 0.19 4 g of 3-maleimidopropionic acid and 0.479 mL of triethylamine were added to the prepared solution. The resulting mixed solution was stirred at room temperature for 48 hours. In addition, the solvent was removed from the mixed solution using a rotary evaporator. The resulting product was dissolved in deionized water again and dialyzed in excess deionized water for 24 hours to conduct primary purification. Then, the primarily purified product was filtered through filter paper. The undesired precipitate was removed from the primarily purified product by the filtration to obtain maleimide-modified TWEEN 80 as a secondarily purified product.

Preparation Example B: Preparation of Target-Specific Magnetic Composite

Example 1

0.1 g of the maleimide-modified TWEEN 80 prepared in the Preparation Example 2 was dissolved in 30 mL of deionized water. 5 mL of a solution containing the magnetic composite prepared in Preparation Example 1 was added to a solution containing the maleimide-modified TWEEN 80 and the mixed solution was stirred at room temperature for 4 hours. In addition, the product obtained by removing the solvent from the mixed solution was dissolved in deionized water again and purified by dialysis in excess deionized water for 2 days.

450 μg of a membrane type-1 matrix metalloproteinase (MT1-MMP) targetable peptide (manufacturer: Peptron) was dissolved in 5 mL of a solution containing the purified product. In addition, the mixed solution was stirred using a vortex for 30 minutes to obtain a target-specific magnetic composite including peptide linked to a magnetic composite via a surfactant.

Test Example A: Characterization of Magnetic Composite

The shape and structure of magnetic composite prepared in Preparation Example 1 were evaluated by a transmission electron microscope (TEM, JEM-1011, JEOL Ltd). A TEM image is shown in FIG. 2. The scale bar of FIG. 2 is 50 nm.

The characteristic bands of the magnetic composite prepared in Preparation Example 1 were confirmed using a Fourier transform-Infrared spectroscope (FT-IR spectrum, Two, Perkin Elmer). The FT-IR spectrum of the magnetic composite (emeraldine base; EB) is shown in FIG. 3. More specifically, i represents C=C and N=Q=N stretching of quinonoid rings at 1,580 cm$^{-1}$, ii represents C=N stretching of quinonoid rings at 1,400 cm$^{-1}$ and 1,495 cm$^{-1}$, and iii represents aromatic C—N stretching of benzenoid rings at 1,300 cm$^{-1}$.

The hydrodynamic size and zeta potential of the magnetic composite prepared in Preparation Example 1 were measured by dynamic light scattering. Results are shown in FIG. 4. In FIG. 4, PMNH is a magnetic composite prepared in Preparation Example 1 and the size of the magnetic composite is about 62.3 nm±8.2 nm.

The absorbance of the magnetic composite prepared in Preparation Example 1 was evaluated using a UV-Vis spectrophotometer (Optizen 2120UV, MECASYS Co.). Results are shown in FIG. 5. As shown in FIG. 5, the magnetic composite did not show absorbance in the case of deionized water (DW) and ethanol (EtOH), but showed significant absorbance in the case of 1-methyl-2-pyrrolidone (NMP). FIG. 5 shows images of solutions containing the magnetic composite in respective solvents.

The sensitivity to magnetic field of the magnetic composite prepared in Preparation Example 1 was evaluated using a vibrating sample magnetometer. Results are shown in FIG. 6. The graph showing a magnetic moment of about zero over the entire field area was a graph of emeraldine salt (ES), and another graph was a graph of emeraldine base (EB).

The magnetic composite was prepared in the same manner as in Preparation Example 1 while changing the concentration of iron. The obtained imaging test results are shown in FIG. 7. FIG. 7 shows results of MR imaging of the corresponding magnetic composite solution according to the concentration of iron. The magnetic composite prepared in Preparation Example 1 had a relaxivity coefficient of 0.738.

Test Example B: Characterization of Target-Specific Magnetic Composite

The hydrodynamic size and zeta potential of the target-specific magnetic composite prepared in Example 1 were measured by dynamic light scattering. Results are shown in FIG. 4. In FIG. 4, PMNHm is a target-specific magnetic composite prepared in Example 1 and the size of the target-specific magnetic composite is about 56.9 nm±2.4 nm.

The presence of a magnetic substance in the target-specific magnetic composite and crystallinity thereof were confirmed by X-ray diffraction. The X-ray diffraction patterns of the target-specific magnetic composite are shown in FIG. 8. In FIG. 8, the symbol (*) represents peaks of magnetic nanoparticles ($Fe_3O_4$).

The MR imaging test of the target-specific magnetic composite was conducted using a 1.5-Tesla clinic MRI device and a micro-47 surface coil (Intera, Philips Medical Systems). Imaging of the target-specific magnetic composite solution was measured at room temperature by CPMG sequence (Carr-Purcell-Meiboom-Gill sequence (TR=4000 ms; TE=20, 40, 80, 100, 120, 140, 160 ms; number of acquisition=2; point resolution—0.156×0.156 mm; section thickness=0.6 mm). Results are shown in FIG. 9. The T2 weighted image showed a change to black due to superparamagnetism of magnetic nanoparticles contained in EB particles, whereas ES magnetic nanoparticles treated with an acid were melted and converted to iron ions and showed no change. The T1 weighted image showed a change to white in ES nanoparticles containing a high amount of iron ions, but showed no change in EB magnetic nanoparticles containing no iron ions.

Test Example C: Analysis of Cell Viability

Human breast cancer MCF7 and fibrosarcoma HT1080 cell lines were cultured in a 10% FBS DMEM medium in a 37° C. humid incubator containing 5% carbon dioxide.

The cell viability of the target-specific magnetic composite of Example 1 with respect to MCF7 and HT1080 cells was assayed by colorimetry based on mitochondrial oxidation of MTT(3-(4,5-dimethylthiazol-2-yl)-2,5-diphenyltetrazolium bromide (Cell Proliferation Kit I, Roche, Germany). In typical cell viability testing, HT1080 and MCF7 cells (each $1 \times 10^4$ cells/well) were seeded on 96-well plates and cultured at a temperature of 37° C. under the atmosphere of 5% carbon dioxide.

The cells were cultured with the target-specific magnetic composite for 4 hours. In addition, the corresponding cells were reacted with a yellow MTT solution for 24 hours. The resulting formazan crystals were solubilized in a solution of 10% sodium dodecyl sulfate in 0.01M HCl.

In addition, the absorbance of the obtained color solution was measured at 584 nm and 650 nm, standard wavelengths, using a microplate spectrophotometer (Epoch™, BioTek, USA). The cell viability was measured as a ratio of the intensity of cells of a group treated with the target-specific magnetic composite to the intensity of cells of a control group not treated with the target-specific magnetic composite. The measurement was repeated four times and the result thus obtained is shown as a mean±standard deviation in FIG. 10. The results indicate that, when a suitable amount of target-specific magnetic composite was administered to MCF7 and HT1080 cells, the cells had almost no cytotoxicity and no problem of cell viability.

Test Example D: In Vitro Redox Detection

In order to measure the absorbance of HT1080 and MCF7 cells ($1 \times 10^4$ cells) cultured with 3.17 mM (based on iron concentration) target-specific magnetic composite of Example 1, these cells were transferred to a cuvette.

The cuvette was placed on a absorbance measurement system between a focusing lens and a quartz-tungsten-halogen light source (Ocean Optics, HL2000) between a collimating lens and a portable spectrometer (Ocean Optics, USB4000). In order to obtain a dark field image of the cells having the target-specific magnetic composite, scattering imaging system was used. The imaging system includes an inverted microscope (Axio Observer Al, CarlZeiss) and a color CCD camera (DCU224C, Thorlabs). Results of Test Example are shown in FIG. 11. In FIG. 11, MCF7(A) shows an image of MCF7 cells cultured together with the target-specific magnetic composite, MCF7(B) shows an image of MCF7 cells not treated with the target-specific magnetic composite, HT1080(A) shows an image of HT1080 cells cultured together with the target-specific magnetic composite, and HT1080(B) shows an image of HT1080 cells not treated with the target-specific magnetic composite. The results indicated that the target-specific magnetic composite has both target-specificity and the capacity to detect the redox state of cancer cells.

Test Example E: In Vivo Model and MR Imaging

All animal tests conducted herein were approved by the Association for Assessment and Accreditation of Laboratory Animal Care International.

In order to obtain a fibrosarcoma orthotopic mouse model, HT1080 cells ($5.0 \times 10^6$ cells) were injected into the proximal thigh of female mice (6 week-old BALB/c-nude mice).

The target-specific magnetic composite of Example 1 was intravenously injected into the tail vein of the mice when the size of cancer reached about 500 $mm^3$.

In vivo MR imaging test was conducted using a 3.0 T clinical MRI device (SIMENS). The following parameters were used for T2-weighted MR imaging.

TR=3,000 ms even echo space
Number of acquisitions=4
Point resolution=192×180 mm
Section thickness=0.1 mm
TE=79 ms In FIG. 12, a) shows the mouse used for testing and part of the mouse on which MR imaging test is conducted. In FIG. 12, b) shows T2 weighted imaging image over time. This shows that a gray part becomes larger than a black part over time and the target-specific magnetic composite is efficiently targeted on the desired part of cancer cells. In addition, in FIG. 12, c) shows a normalized graph of the b) image, a bar graph relates to relaxation time (T2) of a vertical axis, which shows a decrease in the gray part in the b) image, based on, and a curve graph relates to relaxivity (R2), which shows an increase in the black part in the b) image.

Test Example F: Tissue Staining and Imaging

After in vivo MR imaging of Test Example E, hematoxylin and eosin (H&E) staining, and Prussian blue staining were conducted in order to confirm MT1-MMT targeted target-specific magnetic composite in HT1080 cancer cells.

The tissues were dehydrated after alcohol concentration was increased, washed with xylene and dipped in paraffin. The slice tissues having a thickness of 10 µm were set on a glass slide and dipped twice in a container filled with hematoxylin for 10 minutes for nuclear staining. Then, the tissues were washed with water for 10 minutes to remove hematoxylin. In addition, the cytoplasm was stained with eosin and dehydrated in the same manner as described above. After washing three times for 30 minutes, two or three drops of a mount medium were added onto the slide and the slide was covered with a cover slip. In order to visualize presence of the magnetic composite of the cancer cells on the slide, additional staining was conducted using a Prussian blue staining kit. All of the stained tissues were analyzed using a virtual microscope (Olympus BX51, Japan) and Olyvia software. Results are shown in FIG. 13. In FIG. 13, a) shows results of H&E staining and b) shows results of Prussian blue staining. From blue points in b) of FIG. 13, it can be seen that the magnetic composite containing magnetic nanoparticles effectively targeted cancer tissues.

Although the preferred embodiments have been disclosed for illustrative purposes, those skilled in the art will appropriate that various modifications, additions and substitutions are possible, without departing from the scope and spirit of the embodiments as recited in the accompanying claims.

The magnetic composite disclosed herein is used for treating and diagnosing cancers, more superficially, the magnetic composite can be used for detection using magnetic resonance imaging, diagnosis of cancers by a magnetic resonance imaging (MRI) device, and photothermal treatment of cancers and can be used for monitoring removal of cancers while photothermally treating cancers, or can be used for diagnosing removal of cancers after photothermally treating cancers.

In addition, the magnetic composite for treating and diagnosing cancers can be used as an aqueous solution for parenteral administration and a sterile injection preparation. The magnetic composite can be formulated as a sterile injection preparation according to a method well-known in the art.

The invention claimed is:

1. A method of preparing a magnetic composite for treating and diagnosing cancers comprising thermally decomposing a precursor of magnetic nanoparticles in the presence of a conjugated polymer, and
   wherein the conjugated polymer comprises polyaniline, polyacetylene, polypyrrole, polythiophene, poly(p-phenylene vinylene)poly(1,4-phenylene sulfide), poly(fluorenylene ethynylene), a mixture thereof, or a derivative thereof.

2. The method according to claim 1, wherein the precursor of magnetic nanoparticles comprises metal acetylacetonate, metal cupferronate, metal carbonyl, metal chloride, metal sulfide or a mixture thereof.

3. The method according to claim 1, wherein the conjugated polymer is present in an amount of 1 to 1,000 parts by weight, with respect to 100 parts by weight of the magnetic nanoparticles precursor.

4. The method according to claim 1, wherein the thermal decomposition comprises heating a solution containing the conjugated polymer and the precursor of magnetic nanoparticles at a temperature of 100 to 500° C.

5. The method according to claim 1, wherein the thermal decomposition comprises pre-heating the solution containing the conjugated polymer and the precursor of magnetic nanoparticles at a temperature of 100 to 300° C. and heating at a temperature of 200° C. to 500° C.

6. The method according to claim 1, further comprising:
   processing the magnetic composite after the thermal decomposition.

7. The method according to claim 6, wherein the processing comprises treating the magnetic composite with a surfactant.

8. The method according to claim 6, wherein the processing comprises mixing the magnetic composite with a bio-ligand.

* * * * *